(12) United States Patent
Hori et al.

(10) Patent No.: US 6,730,776 B1
(45) Date of Patent: May 4, 2004

(54) WF14573 OR ITS SALT, PRODUCTION THEREOF AND USE THEREOF

(75) Inventors: Yasuhiro Hori, Tokyo (JP); Shigehiro Takase, Ishioka (JP); Yasuhisa Tsurumi, Tsukuba (JP); Michizane Hashimoto, Tsuchiura (JP); Motohiro Hino, Tsuchiura (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/646,342
(22) PCT Filed: Mar. 12, 1999
(86) PCT No.: PCT/JP99/01235
§ 371 (c)(1),
(2), (4) Date: Sep. 18, 2000
(87) PCT Pub. No.: WO99/47551
PCT Pub. Date: Sep. 23, 1999

(30) Foreign Application Priority Data

Mar. 16, 1998 (AU) .............................. PP-2349
Apr. 29, 1998 (AU) .............................. PP-3256

(51) Int. Cl.⁷ ................................ C07K 7/50
(52) U.S. Cl. .................... 530/317; 514/11; 514/16; 530/329
(58) Field of Search ................. 530/317, 324; 514/11, 16

(56) References Cited

FOREIGN PATENT DOCUMENTS

| EP | 0561639 | * | 9/1993 |
| EP | 0644199 | * | 3/1995 |

OTHER PUBLICATIONS

Adam (Medicine 65, 203, 1986).*
Berman, Judith (Nat Rev Genet 3 (12) 918–30, 2002).*
Bhalodia M V (Journal of the Association for Academic Minority Physicians 9 (4) 69–71, 1998).*
Buchta, V. (Mycoses 44 (11 12) 505–12, 2001).*
Garbino (Medicine 81 (6) 425–33, 2002).*
Krcmery V. (Journal of Chemotherapy 11 (5) 385–90, 1999).*
Manfredi R (Mycopathologia 148 (2) 73–8, 1999).*
Marr K. A. (Antimicrobial Agents and Chemotherapy 45 (1) 52–9, 2001).*
Moore M. L. (Journal of Perinatology 21 (6) 399–401, 2001).*
Nagasawa M. (Journal of Infection 44 (3) 198–201, 2002).*
van Duin David (Antimicrobial Agents and Chemotherapy 46 (11) 3394–400, 2002).*
Vilchez Regis A (Am J Transplant 2 (7) 575–80, 2002).*
Wang M. X. (Cornea 19 (4) 558–60, 2000).*

* cited by examiner

Primary Examiner—Christopher S. F. Low
Assistant Examiner—David Lukton
(74) Attorney, Agent, or Firm—Oblon, Spivak, McClelland, Maier & Neustadt, P.C.

(57) ABSTRACT

The present invention provides a new antimicrobial compound WF14573, and a process for producing WF14573 by (a) culturing a WF14573A and/or B-producing microorganism in a nutrient medium and recovering WF14573A and/or B from the resultant cultured broth or (b) deacylating WF14573A and/or B in the presence of a microbial substance which is capable of deacylating WF14573A and/or B. Also provided are an antimicrobial agent comprising WF14573 and carrier(s), a pharmaceutical composition comprising an effective amount of WF14573 and pharmaceutically acceptable carrier(s), a method for killing microorganisms by applying WF14573 to the microorganisms, and use of WF14573 for the treatment of infectious diseases caused by pathogenic microorganisms.

28 Claims, No Drawings

WF14573 OR ITS SALT, PRODUCTION THEREOF AND USE THEREOF

TECHNICAL FIELD

This invention relates to a new antimicrobial compound, WF14573 or its salt. More particularly, it relates to a new antimicrobial compound, WF14573 or its salt which has an antimicrobial activity against pathogenic microorganisms, especially pathogenic fungi, a process for the preparation thereof and a pharmaceutical composition comprising the same.

DISCLOSURE OF INVENTION

The new compound, WF14573 is represented by the following formula:

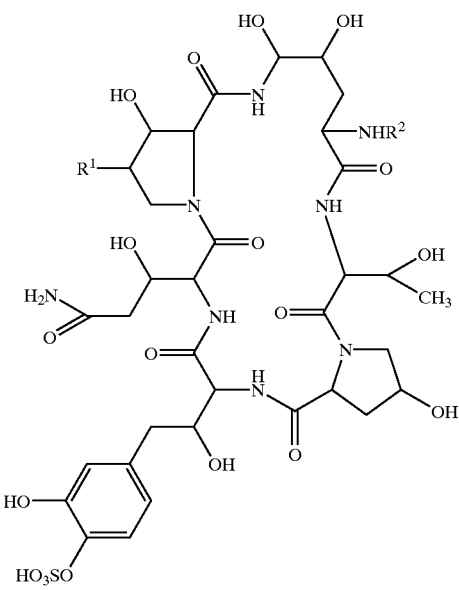

wherein $R^1$ is hydrogen or methyl and $R^2$ is hydrogen or palmitoyl.

In this specification, the following designations of the specific compound are conveniently used.

| Compound name | $R^1$ | $R^2$ |
|---|---|---|
| WF14573 A | —H | —CO(CH$_2$)$_{14}$CH$_3$ |
| WF14573 B | —CH$_3$ | —CO(CH$_2$)$_{14}$CH$_3$ |
| Deacyl WF14573 A | —H | —H |
| Deacyl WF14573 B | —CH$_3$ | —H |

The new compound, WF14573A has the following physico-chemical properties:
a) Molecular weight: ESI-MS(negative)m/z 1143 (M–H); b) Elemental analysis: C 48.39; H 7.15; N 8.95; c) Melting point: 230–240° C. (dec.); d) Optical rotation: $[\alpha]_D^{23}$=−12 (c 0.5, methanol); e) UV spectrum: λ max(ε)=276 nm (methanol); f) IR spectrum: ν max(KBr)=3360, 2920, 2830, 1670, 1630, 1540, 1440, 1270, 1240, 1050 cm$^{-1}$; g) $^1$H-NMR spectrum: (500 MHz, CD$_3$OD) δ (ppm): 7.18 (1H, d, J=8 Hz), 6.80 (1H, d, J=2 Hz), 6.67 (1H, dd, J=8, 2 Hz), 5.30 (1H, d, J=3 Hz), 5.10 (1H, d, J=4 Hz), 4.98 (1H, d, J=3 Hz), 4.64 (1H, m), 4.58~4.52 (3H, m), 4.47~4.43 (2H, m), 4.40~4.33(2H, m), 4.27 (1H, d, J=3 Hz), 4.02~3.95 (3H, m), 3.82~3.76 (2H, m), 2.70 (1H, m), 2.63~2.55 (2H, m), 2.48~2.40 (2H, m), 2.30~2.17 (3H, m), 2.05~1.93(4H, 1.57 (2H, m), 1.35~1.23 (24H, m), 1.15 (3H, d, J=6 Hz), 0.89 (3H, t, J=7 Hz). h) $^{13}$C-NMR spectrum: (125 MHz, CD$_3$OD) δ (ppm): 176.8 (s), 175.9 (s), 174.4 (s), 174.1 (s), 172.9 (s), 172.7 (s), 172.5 (s), 169.3 (s), 150.3 (s), 140.1 (s), 137.6 (s), 124.0 (d), 121.9 (d), 119.4 (d), 74.2 (d), 74.0 (d), 73.9 (d), 71.3 (d), 70.7 (d), 70.5 (d), 69.8 (d), 68.3(d) 62.4 (d), 58.5 (d), 58.0 (d), 57.2 (t), 55.4 (d), 51.2 (d), 47.0 (t), 41.1 (t), 39.7 (t), 38.9 (t), 36.7 (t), 35.0 (t), 34.6 (t), 33.1(t), 30.80 (t×5), 30.76 (t), 30.7 (t), 30.6 (t), 30.5 (t), 30.3 (t), 27.0 (t). 23.7 (t), 19.5 (q), 14.4 (q). i) Solubility; Soluble: water, methanol. dimethylsulfoxide; Insoluble: n-hexane, chloroform; j) Thin layer chromatography: Carrier: Silica gel 60 F254 (Merck); Solvent: 1-butanol: acetic acid: water=4:1:2; Rf=0.39.

The new compound, WF14573B (as its sodium salt), has the following physico-chemical properties:
a) Molecular weight: ESI-MS(negative)m/z 1157 (M–H); b)Elemental analysis: C 48.79; H 7.34; N 8.96; S 2.80; Na 1.69; c) Melting point: 220–225° C. (dec.); d)Optical rotation: $[\alpha]_D^{23}$=15° (c 0.9, methanol); e) UV spectrum: λ max(ε)=276 nm (methanol); f) IR spectrum: ν max(KBr)= 3360, 2940, 2830, 1670, 1630, 1530, 1440, 1270, 1240, 1050 cm$^{-1}$; g) $^1$H-NMR spectrum: (500 MHz, CD$_3$OD) δ (ppm): 7.18 (1H, d, J=8 Hz), 6.80 (1H, d, J=2 Hz), 6.67 (1H, dd, J=8, 2 Hz), 5.29 (1H, d, J=3 Hz), 5.07 (1H, d, J=4 Hz), 4.99 (1H, d, J=4 Hz), 4.64 (1H, m), 4.58~4.51 (3H, m), 4.48~4.36 (4H, m), 4.16 (1H, m), 4.07 (1H, m), 4.02~3.97 (2H, m), 3.79 (1H, br. d, J=11 Hz), 3.37 (1H, m), 2.69 (1H, m), 2.60~2.40 (5H, m), 2.22 (2H, m), 2.05~1.98 (3H, m), 1.57 (2H, m), 1.35~1.24 (24H, m), 1.15 (3H, d, J=6 Hz),1.06 (3H, d, J=7 Hz), 0.89 (3H, t, J=7 Hz). h) $^{13}$C-NMR spectrum: (125 MHz, CD$_3$OD) δ (ppm): 176.7 (s), 176.0 (s), 174.3 (s), 174.1 (s), 172.8 (s), 172.5 (s), 172.5 (s), 169.3 (s), 150.3 (s), 140.1 (s), 137.6 (s), 124.0 (d), 122.0 (d), 119.4 (d), 75.9 (d), 74.0 (d), 73.9 (d), 71.3 (d), 70.7 (d), 70.5 (d), 70.2 (d), 68.2 (d), 62.4 (d), 58.6 (d), 58.0 (d), 57.2 (t), 55.5 (d), 52.9 (t), 51.3 (d), 41.1 (t), 39.8 (t), 39.1 (d), 38.9 (t), 36.7 (t), 34.9 (t), 33.0 (t), 30.8 (t×5), 30.7 (t), 30.7 (t), 30.5 (t), 30.4 (t), 30.3 (t), 27.0 (t), 23.7 (t), 19.5 (q), 14.4 (q), 11.1 (q). i) Solubility; Soluble: water, methanol, dimethylsulfoxide; Insoluble: n-hexane, chloroform; j) Thin layer chromatography: Carrier: Silica gel 60 F254 (Merck); Solvent: 1-butanol: acetic acid: water=4:1:2; Rf=0.45.

In the result of the above physicochemical properties and extensive investigations, the chemical structures of WF14573A and B are identified as mentioned above, respectively.

BEST MODE FOR CARRYING OUT OF THE INVENTION

According to this invention, the compound, WF14573A and B can be prepared by culturing a WF14573A and/or B-producing strain belonging to the genus Coleophoma in a nutrient medium.

Particulars of microorganisms used for the production of WF14573A and B and production thereof will be explained in the followings.

Microorganism

The microorganism which can be used for the production of WF14573A and B is a WF14573A and/or B-producing strain belonging to the genus Coleophoma, among which *Coleophoma empetri* No.14573 was newly isolated from a decayed leaf sample, collected at Mitsushima-cho, Kamiagata-gun, Nagasaki-ken, Japan.

Lyophilized samples of the newly isolated microorganism, *Coleophoma empetri* No. 14573 was deposited with an International Depository Authority on the Budapest Treaty, National Institute of Bioscience and Human-Technology, 1–3. Higashi 1-chome, Tsukuba-shi, Ibaraki-ken, 305, Japan under the deposit number FERM BP-6252 on Feb. 12, 1998.

It is to be understood that the production of the new compound, WF14573A and/or B is not limited to the use of the particular organism described herein, which is given for illustrative purpose only. This invention also includes the use of any mutants which are capable of producing the WF14573A and/or B including natural mutants as well as artificial mutants which can be produced from the described organism by conventional means, such as genetic engineering, X-ray, ultraviolet radiation, treatment with N-methyl-N'-nitro-N-nitrosoguanidine and the like.

The strain No.14573 has the following morphological, cultural and physiological characteristics.

The strain grew rather restrictedly on various culture media, and formed grayish colonies. The strain produced pycnidial to stromatic conidiomata on the autoclaved leaf segments affixed on agar media, while it formed neither teleomorph nor anamorph on or in the media. The conidiomata were convex to discoid, dark brown to black, and formed ampulliform to lageniform conidiogenous cells on the lower cells of their inner walls. Conidia were hyaline, one-celled and cylindrical. On the basis of comparing the morphological characteristics with fungal taxonomic criteria by von Arx (J. A. von Arx: The Genera of Fungi—Sporulating in Pure Culture. 3rd ed., pp.315, J. Cramer, Vaduz, 1974) and by Sutton (B. C. Sutton: The Coelomycetes—Fungi Imperfecti with Pycnidia, Acervuli and Stroma., pp.696, Commonwealth Mycological Institute, Kew, 1980), strain No.14573 was considered to belong to the coelomycete genus Coleophoma Höhn. 1907 (Sphaeropsidales). Its mycological characteristics were as follows.

Cultural characteristics on various agar media are summarized in Table 1. Culture on potato dextrose agar grew restrictedly, attaining 1.5–2.5 cm in diameter two weeks later at 25° C. This colony surface was plane to raised, felty to cottony, light gray to dark gray, and yellowish white at the margin. The reverse color was olive. Conidial structures were not observed. Colonies on corn meal agar grew rather restrictedly, attaining 2.5–3.5 cm in diameter under the same conditions. The surface was plane to centrally raised, dark gray and lustrous. At the colony center was felty to cottony and purplish gray to dark purple. Mycelium near the margin was submerged and white. The reverse was dark gray to dark green, and yellowish white at the margin. Conidial structures were not produced.

The morphological characteristics were determined from the cultures on the sterile leaf segments affixed on a Miura's LCA plate (Miura, K. and M. Kudo: *Trans. Mycol. Soc. Japan*. 11:116–118, 1970). Conidiomata formed on the leaf segments alone. They were pycnidial to stromatic, superficial to semi-immersed, separate and dark brown to black. Their shape was convex to discoid, sometimes papillate, non-ostiolate or indistinctly ostiolate, unilocular, flattened at the base, thin-walled at the upper part, 70–170 μm in diameter and 40–90 μm high. The lower cells of inner pycnidial walls were thick-walled, dark brown, irregularly shaped, and formed textura angularis. The inner cells produced directly conidiogenous cells, but they sometimes formed conidiophores. The conidiophores were hyaline, smooth, septate, simple to sparingly branched, and 10–17× 3.5–4.5 μm. The conidiogenous cells were discrete, acrogenous or intercalary, hyaline, smooth, ampulliform to lageniform, sometimes cylindrical, and 5–11(–16)×2–4.5 μm. Conidia were holoblastic, hyaline, smooth, one-celled, cylindrical, rounded at the apical end, with a small projection at the base, and (11–)13–20×2–3 μm. Paraphyses were often formed on or amongst conidiophores, and their structures were similar to sheaths covering with conidiogenous cells and conidia. They were hyaline, thin-walled, campanulate to cylindrical, collapsing at later stage, and 18–30(–35)× 2.5–5 μm. Vegetative hyphae were smooth, septate, brown and branched. The hyphal cells were cylindrical and 2–7 μm in width. Chlamydospores were not observed.

Strain No.14573 was able to grow at the temperature range from 3 to 30° C., with the growth optimum at 21 to 24° C. These temperature data were determined on potato dextrose agar (made by NISSUI).

According to the taxonomic criteria of the genus Coleophoma by Wu et al. (W. Wu, B. C. Sutton and A. C. Gange: *Mycol. Res.* 100: 943–947. 1996.), the strain No.14573 resembles *Coleophoma empetri* (Rostr.) Petrak 1929. There were few differences between above characteristics and this species description: superficial and indistinctly ostiolate conidiomata. Added to these, it remains one question for the structures described as paraphyses. Much more observation was needed to determine the conidial ontogeny of this genus. In conclusion, we identified the isolate as one strain of *Coleophoma empetri*, and named it *Coleophoma empetri* No. 14573.

TABLE 1

Cultural characteristics of strain No. 14573.

| Media | Cultural characteristics |
|---|---|
| Malt extract agar* | G: Very restrictedly, 1.0–2.0 cm<br>S: Circular, plane, felty, formed no anamorph, brownish gray (5F2) to grayish brown (6F3)<br>R: Olive (3F4) to olive brown (4F4), and olive (3E3–3E4) at the center |
| Potato dextrose agar (Difco 0013) | G: Restrictedly, 1.5–2.5 cm<br>S: Circular, plane to raised, felty to cottony, formed no anamorph, light gray (1D1) to dark gray (1F1), yellowish white (3A2) at the margin<br>R: Olive (3D3–3F3) |
| Czapek's solution agar* | G: Restrictedly, 1.5–2.5 cm<br>S: Circular, submerged, thin, plane, formed no anamorph, olive brown (4F4)<br>R: Olive brown (4F4) |
| Sabouraud dextrose agar (Difco 0190) | G: Restrictedly, 1.5–2.5 cm<br>S: Circular, plane to centrally raised, felty, partly hygroscopic, sectoring, formed no anamorph, orange white (5A2) to grayish yellow (4C4), dark gray (1F1) at the center and sectors<br>R: Grayish yellow (4B4–4C3), and brownish gray (5F2) at the center and sectors |
| Emerson Yp Ss agar (Difco 0739) | G: Restrictedly, 2.0–3.0 cm<br>S: Circular, plane, felty, formed no anamorph, gray (1F1) to olive gray (1F2), yellowish white (3A2) at the margin<br>R: Greenish gray (25F2) to dark green (25F3), and yellowish white (3A2) at the margin |
| Corn meal agar (Difco 0386) | G: Rather restrictedly, 2.5–3.5 cm<br>S: Circular, plane to centrally raised, formed no anamorph, lustrous, dark gray (1F1): felty to cottony, purplish gray (14F2) to dark purple (14F3) at the center; submerged and white (1A1) at the margin<br>R: Dark gray (1F1) to dark green (25F3), yellowish white (3A2) at the margin |

TABLE 1-continued

Cultural characteristics of strain No. 14573.

| Media | Cultural characteristics |
|---|---|
| MY20 agar* | G: Very restrictedly, 1.0–2.0 cm<br>S: Circular, plane, hygroscopic, lustrous, formed no anamorph, grayish yellow (4B3)<br>R: Light yellow (4A4–4A5) |
| Oatmeal agar (Difco 0552) | G: Rather rapidly, 3.0–4.0 cm<br>S: Circular, plane to centrally raised, felty to cottony, formed no anamorph, dark gray (1F1), and yellowish white (4A2) at the margin |

Abbreviation G: growth, measuring colony size in diameter, S: colony surface, R: reverse.
*The compositions of malt extract agar, Czapek's solution agar and MY20 agar were based on JCM Catalogue of Strains (Nakase, T., 6th ed., pp617., Japan Collection of Microorganisms, the Institute of Physical and Chemical Research, Saitama, 1995).

These characteristics were observed after 14 days of incubation at 25° C. The color descriptions were based on Methuen Handbook of Colour (Kornerup, A. and J. H. Wanscher, 3rd ed., pp.252., Methuen, London, 1978).

Production of WF14573A and B

The compound, WF14573A and B can be prepared by culturing a WF14573A and/or B-producing strain in a nutrient medium.

In general, WF14573A and B can be produced by culturing the WF14573A and/or B-producing strain in a nutrient medium containing assimilable sources of carbon and nitrogen, preferably under aerobic conditions (e.g. shaking culture. submerged culture, etc.).

The preferred sources of carbon are carbohydrates such as sucrose, glucose, soluble starch and the like.

The preferred sources of nitrogen are cottonseed meal, soybean flour, yeast extract, peptone, gluten meal, corn steep liquor, dried yeast etc. as well as inorganic and organic nitrogen compounds such as ammonium salts (e.g. ammonium nitrate, ammonium sulfate, ammonium phosphate, etc.), urea, amino acid and the like.

The carbon and nitrogen sources need not be used in their pure form, because less pure materials which contain traces of growth factors and considerable quantities of mineral nutrients, are also suitable for use. Further, there may be added to the medium. Mineral salts such as calcium carbonate, sodium or potassium phosphate magnesium salts and the like. If the culture medium is foamed remarkably, a defoaming agent such as liquid paraffin, higher alcohol, plant oil, mineral oil and silicones may be added.

Preferred production conditions of WF14573A and/or B in massive amount may includes a submerged aerobic cultural condition.

Preferred production conditions of WF14573A and/or B in small amount may include a shaking or surface culture in flask or bottle.

In case where the production is carried out in a large tank, it is preferable to use the vegetative form of the organism for inoculation in the production tank in order to avoid growth lag.

Agitation and aeration of the culture broth may be accomplished in a variety of ways. Agitation may be provided by a propeller or the similar mechanical agitation equipment, by revolving or shaking the fermentor, by various pumping equipment or by the passage of sterile air through the medium.

The fermentation is usually conducted at a temperature between 20° C. and 35° C., preferably about 25° C. for 50 to 100 hours, which may be varied depending on the fermentation condition and scale.

Thus produced WF14573A and B can be recovered from the cultured broth by conventional means which are commonly used for the recovery of other fermentation products such as antibiotics.

In general, most of the WF14573A and B produced are found in the culture filtrate as well as in the cells. Accordingly, WF14573A and B can be isolated from the filtrate and the cells, which is obtained by filtering or centrifuging the broth, by a conventional method such as concentration under reduced pressure, lyophilization, extraction with a solvent, pH adjustment, treatment with a resin (e.g. anion or cation exchange resin, non-ionic adsorption resin), treatment with an adsorbent (e.g. activated charcoal, silicic acid, silica gel, cellulose, alumina), crystallization, recrystallization and the like. The WF14573A and B obtained in its free form may also be converted to its salts by treating WF14573A and B with an inorganic or organic base such as sodium or potassium hydroxide, ammonium hydroxide, ethanolamine and the like and with an amino acid such as glycine, lysine, glutamic acid and the like.

The WF14573 and B have a strong antimicrobial activity against pathogenic microorganisms, especially pathogenic fungi such as pathogenic yeast (e.g. *Candida albicans* etc.) and the like. Accordingly, the WF14573A and B and their pharmaceutically acceptable salt are useful as an antimicrobial agent, especially antifungal agent which is used for the treatment of infectious diseases in human beings and animals.

As examples for showing such pharmacological effects of WF14573A and B, some pharmacological test data are illustrated in the followings.

Test 1 (Antimicrobial Activity)

Antimicrobial activity of WF14573A or B was determined by a serial broth dilution method using 96-well microtiter plate in 100 μl of veast nitrogen base dextrose medium. The inoculum was adjusted to $1\times10^5$ colony forming units/ml. *Candida albicans* and *Aspergillus fumigatus* were cultured at 37° C. for 24 hours and *Cyptococcus neoformans* was cultured at 37° C. for 48 hours in 5% $CO_2$ incubator. After incubation, the growth inhibition of microorganism in each well was determined by microscopic observation. The results were shown as MEC (minimum effective concentration: μg/ml) value (Table 1).

TABLE 1

Antimicrobial activity of WF14573A and B.

| | MEC (μg/ml) | |
|---|---|---|
| Microorganisms | WF14573A | WF14573B |
| *Candida albicans* FP633 | 0.31 | 0.04 |
| *Aspergillus fumigatus* FP1305 | 0.08 | 0.02 |
| *Cryptococcus neoformans* YC203 | 50.0 | 50.0 |

The deacyl WF14573A or B or their salts can be prepared by deacylating WF14573A or B or their salts, especially by deacylating WF14573A or B or their salts respectively, in the presence of cultured broth or its processed material of a microoranism [such as a microorganism belonging to the genus Streptomyces, e.g. *Streptomyces anulatus* No. 4811 (FERM BP-5808)] which is capable of deacylating WF14573A or B to give deacyl WF14573A or B.

The processed material of the cultured broth may include mycelia and crude or purified deacylase preparations obtained from them.

The enzymatic reaction is carried out in a conventional manner, e.g. those described in the following working Examples.

The deacyl WF14573A or B can be converted to an acyl derivative thereof by a conventional acylation. The acyl derivative can be represented by the above formula (I) wherein $R^2$ is acyl except palmitoyl.

The present antimicrobial agent comprising the WF14573 (I) or pharmaceutically acceptable salt thereof is useful as a therapeutic agent for infectious diseases in animals including human beings. The pharmaceutically acceptable salt of the WF14573 (I) may include the salt as exemplified above.

The antimicrobial composition can be used in the form of pharmaceutical preparation, for example, in solid, semisolid or liquid form, which contains the WF14573 (I) or its salt in admixture with a pharmaceutical organic or inorganic carrier or excipient suitable for external, enteral or parenteral applications. The active ingredient may be compounded, for example, with usual non-toxic, pharmaceutically acceptable carriers for tablets, pellets, capsules, suppositories, solutions, emulsions, suspensions, ointments and any other form suitable for use. The pharmaceutically acceptable carriers are water, glucose, lactose, gum acacia, gelatin, mannitol, starch paste, magnesium trisilicate, talc, corn starch, keratin, colloidal silica, potato starch, urea and other carriers suitable for use in manufacturing preparations and in addition, auxiliary, stabilizing, thickening and coloring agents and perfumes. The antimicrobial compositions can also contain preserving or bacteriostatic agents thereby keeping the active ingredient in the desired preparations stable in activity. The active object compound is contained in the antimicrobial composition in an amount sufficient to produce the desired therapeutic effect upon the bacterially infected process or condition.

For applying this composition to human patients, it is preferably to apply it in a form of intraveneous, intramuscular, oral or percutaneous administration. While the dosage or therapeutically effective amount of the WF14573 (I) or pharmaceutically acceptable salts thereof varies depending on the age, conditions of each individual patient to be treated, the preferred daily dosage of the WF14573 (I) can be selected from the range of 0.1–100 mg/kg of the patient.

The following Examples are given for the purpose of illustrating this invention, but not limited thereto.

EXAMPLE 1

(1) Fermentation of *Coleophoma empetri* No. 14573 for the Production of the WF14573A An aqueous seed medium (30 ml) containing sucrose 4%, glucose 1%, soluble starch 2%, cottonseed meal 3%, soybean flour 1.5%, $KH_2PO_4$ 1%, $CaCO_3$ 0.2%, Adecanol LG-109 (defoaming agent, Asahi Denka Co., Ltd.) 0.05%, and Silicone KM-70 (defoaming agent, Shin-Etsu Chemical Co., Ltd.) 0.05% was placed in each of three 100-ml Erlenmeyer flasks and was sterilized at 120° C. for 30 minutes. A loopful of *Coleophoma empetri* No. 14573, grown on YpSs agar at 25° C. for 2 weeks, was inoculated in each of the seed flasks. The inoculated flasks were shaken on a rotary shaker (220 rpm, 5.1 cm throw) at 25° C. for 5 days, and 8 ml of the seed culture were transferred to 160 ml of the same sterile seed medium in the 500-ml Erlenmeyer flasks. The flasks were shaken on a rotary shaker (220 rpm, 5.1 cm throw) at 25° C. for 2 days, and 640 ml (four flasks) of the second seed culture were inoculated to 20 liters of sterile production medium consisting of modified starch 5%, cottonseed meal 2%, oat meal 0.5%, $KH_2PO_4$ 3.5%, $Na_2HPO_4.12H_2O$ 2.63%, $(NH_4)_2SO_4$ 0.6%, L-isoleucine 0.5%, L-proline 0.5%, Adecanol LG-109 0.05%, and Silicone KM-70 0.05% in a 30-liter jar fermentor. Fermentation was carried out at 25° C. for 5 days under aeration of 20 liters/minute and agitation of 250 rpm.

The production of the WF14573A in the fermentation broth was monitored by HPLC analysis indicated below.

analytical HPLC condition; column: YMC Pack ODS-AM 303, S-5 120A (250×4.6 mm I.D., YMC Co., Ltd.); mobile phase: 50% aqueous acetonitrile containing 0.1% TFA; flow rate: 1 ml/min. detection: UV at 210 nm; retention time: WF14573A 11.9 min.

(2) Isolation and Purification of the WF14573A

The culture broth (80 liters) was extracted with an equal volume of acetone by stirring for 2 hours at room temperature. The mixture was filtered with an aid of diatomaceous earth. The filtrate was diluted with an equal volume of water and passed through a column (6 L) of DIAION HP-20 (Mitsubishi Chemical Co., Ltd.) packed with water. The column was washed with 50% aqueous methanol (19 L) and then eluted with methanol (34 L). The active fraction (0–20 L) was diluted with an equal volume of water and passed through a column (4 L) of YMC-GEL (ODS-AM 120-S50, YMC Co., Ltd.) packed with 50% aqueous methanol. The column was washed with 50% (6.5 L) and 60% aqueous methanol (12L) and then eluted with 70% aqueous methanol (15.9 L). The active fraction (5.8–15.9 L) was concentrated in vacuo to 5.3 L. One liter of this solution was diluted with an equal volume of water and passed through a column (1 L) of YMC-GEL (ODS-AM 120-S50, YMC Co., Ltd.) packed with 20% aqueous methanol. The column was washed with 40% aqueous acetonitrile containing 0.5% $NH_4H_2PO_4$ (3 L) and eluted with 50% aqueous acetonitrile containing 0.5% $NH_4H_2PO_4$ (2.9 L). The active fraction (1.05–1.35 L) was diluted with an equal volume of water and passed through a column (2 L) of YMC-GEL (ODS-AM 120-S50, YMC Co., Ltd.) packed with 25% aqueous acetonitrile. The column was washed with 40% aqueous methanol and eluted with 80% aqueous methanol. The active fraction was concentrated in vacuo to an aqueous solution and lyophilized to give 798 mg of crude WF14573A. This powder was dissolved in a small volume of water and further purified by preparative HPLC, using YMC-packed column (ODS-AM SH-343-5AM S-5, 250×20 mm I.D., YMC Co., Ltd.) with 50% aqueous acetonitrile containing 0.5% $NaH_2PO_4.2H_2O$ as a mobile phase. A flow rate was 9.9 ml/minute. Fractions containing the WF14573A were collected. These active fractions were diluted with an equal volume of water and passed through YMC-packed column (ODS-AM SH-343-5AM S-5, 250×20 mm I.D., YMC Co., Ltd.) equilibrated with 25% aqueous acetonitrile containing 0.25% $NaH_2PO_4.2H_2O$. The column was washed with 30% aqueous methanol and then eluted with 70% aqueous methanol at a flow rate of 9.9 ml/minute. The eluate was concentrated in vacuo and lyophilized to give 121 mg of WF14573A as white powder.

EXAMPLE 2

(1) Fermentation of *Coleophoma empetri* No. 14573 for the Production of the WF14573B An aqueous seed medium (30 ml) containing sucrose 4%, glucose 1%, soluble starch 2%, cottonseed meal 3%, soybean flour 1.5%, $KH_2PO_4$ 1%, $CaCO_3$ 0.2%, Adecanol LG-109 (defoaming agent, higher alcohol, Asahi Denka Co., Ltd.) 0.05%, and Silicone KM-70 (defoaming agent, Shin-Etsu Chemical Co., Ltd.) 0.05% was placed in each of three 100-ml Erlenmeyer flasks and was sterilized at 120° C. for 30 minutes. A loopful of Coleophoma empetri No. 14573, grown on YpSs agar at 25° C. for 2 weeks, was inoculated in each of the seed flasks. The inoculated flasks were shaken on a rotary shaker (220 rpm, 5.1 cm throw) at 25° C. for 5 days, and 8 ml of the seed culture was transferred to 160 ml of the same sterile seed medium in the 500-ml Erlenmeyer flasks. The flasks were shaken on a rotarv shaker (220 rpm, 5.1 cm throw) at 25° C. for 2 days, and 640 ml (four flasks) of the second seed culture was inoculated to 20 liters of sterile production medium consisting of sucrose 8%, dried yeast 4%, $CaCO_3$ 0.5%, Adecanol LG-109 0.05%, and Silicone KM-70 0.05% (pH 6.3 adjusted with 1N NaOH) in a 30-liter jar fermentor. Fermentation was carried out at 25° C. for 5 days under aeration of 20 liters/minute and agitation of 250 rpm.

The production of the WF14573B in the fermentation broth was monitored by HPLC analysis indicated below.

analytical HPLC condition; column: YMC Pack ODS-AM 303, S-5 120A (250×4.6 mm I.D., YMC Co., Ltd.); mobile phase: 50% aqueous acetonitrile containing 0.1% TFA; flow rate: 1 ml/min. detection: UV at 210 nm; retention time: WF14573B 13.2 min.

(2) Isolation and Purification of the WF14573B

The culture broth (40 liters) was extracted with an equal volume of acetone by stirring for 2 hours at room temperature. The mixture was filtered with an aid of diatomaceous earth. The filtrate was diluted with an equal volume of water and passed through a column (3 L) of DIAION HP-20 (Mitsubishi Chemical Co., Ltd.) packed with water. The column was washed with water (9 L) and 50% aqueous methanol (10 L) and then eluted with methanol (29 L). The active fraction (0–20 L) was diluted with an equal volume of water and passed through a column (1 L) of YMC-GEL (ODS-AM 120-S50, YMC Co., Ltd.) packed with water. The column was washed with 60% (5 L) and 70% (2.8 L) aqueous methanol and then eluted with 80% aqueous methanol (2.8 L). The active fraction (0.8–2.8 L) was diluted with an equal volume of water and passed through a column (1 L) of YMC-GEL (ODS-AM 120-S50, YMC Co., Ltd.) packed with water. The column was washed with 40% aqueous methanol (1 L) and eluted with 50% aqueous acetonitrile containing 0.5% $NH_4H_2PO_4$ (3.3 L). The active fraction (2.0–2.5 L) was diluted with an equal volume of water and passed through a column (2 L) of YMC-GEL (ODS-AM 120-S50, YMC Co., Ltd.) packed with water. The column was washed with 40% aqueous methanol (6 L) and eluted with 80% aqueous methanol (4.35 L). The active fraction (2.5–4.35 L) was concentrated in vacuo to an aqueous solution and lyophilized to give 411 mgofcrude WF14573B. A part of this powder (120 mg) was dissolved in a small volume of water and further purified by preparative HPLC, using YMC-packed column (ODS-AM SH-343-5AM S-5, 250×20 mm I.D., YMC Co., Ltd.) with 50% aqueous acetonitrile containing 0.5% $NaH_2PO_4.2H_2O$ as a mobile phase. A flow rate was 9.9 ml/minute. Fractions containing the WF14573B were collected. These active fractions were diluted with an equal volume of water and passed through YMC-packed column (ODS-AM SH-343-5AM S-5, 250×20 mm I.D., YMC Co., Ltd.) equilibrated with 25% aqueous acetonitrile containing 0.25% $NaH_2PO_4.2H_2O$. The column was washed with 30% aqueous methanol (240 ml) and then eluted with 80% aqueous methanol at a flow rate of 9.9 ml/minute. The eluate was concentrated in vacuo and lyophilized to give 70 mg of WF14573B as white powder.

EXAMPLE 3

Preparation of Deacyl WF14573A (1) Fermentation of Streptomyces anulatus No. 4811 (FERM BP-5808)

A stock culture of Streptomyces anulatus No.4811 was prepared and maintained on an agar slant. A loopful of the slant culture was inoculated into 60 ml of sterilized seed medium consisting of maltose 3%, dried yeast 1%, $CaCO_3$ 0.5% in a 225-ml Erlenmeyer flask. The flask was incubated at 30° C. for 3 days on a rotary shaker (220 rpm, 5.1 cm-throw) and then inoculated (0.1%) into 60 ml of sterilized seed medium consisting of maltose 3%, dried yeast 1%, $CaCO_3$ 0.5%, Adecanol LG-109 (Asahi Denka Co., Ltd.) 0.1% and Silicone KM-70 (Shin-Etsu Chemical Co., Ltd.) 0.1% in each of three 225-ml Erlenmeyer flasks. The flasks were incubated at 30° C. for 2 days on a rotary shaker (220 rpm, 5.1 cm-throw).

The resultant seed culture was then inoculated (5%) into 60 ml of sterilized production medium consisting of maltose 8%, soybean meal 2%, wheat germ 2%, potato protein 2%, $CaCO_3$ 0.5%, Adecanol LG-109 0.1% and Silicone KM-70 0.1% in each of fifty 225-ml Erlenmeyer flasks. The flasks were incubated at 30° C. for 6 days on a rotary shaker (220 rpm, 5.1 cm-throw). The vegetative mycelia were collected from the fermented broth by filtration and once washed with water. The washed mycelia were used to obtain the deacyl WF14573A.

(2) Fermentation of Coleophoma empetri No. 14573 for the Production of the WF14573A An aqueous seed medium (30 ml) containing sucrose 4%, glucose 1%, soluble starch 2%, cottonseed meal 3%, soybean flour 1.5%, $KH_2PO_4$ 1%, $CaCO_3$ 0.2%, Adecanol LG-109 (defoaming agent, Asahi Denka Co., Ltd.) 0.05%, and Silicone KM-70 (defoaming agent, Shin-Etsu Chemical Co., Ltd.) 0.05% was placed in each of three 100-ml Erlenmeyer flasks and was sterilized at 120° C. for 30 minutes. A loopful of Coleophoma empetri No. 14573, grown on YpSs agar at 25° C. for 2 weeks, was inoculated in each of the seed flasks. The inoculated flasks were shaken on a rotary shaker (220 rpm, 5.1 cm throw) at 25° C. for 5 days, and 8 ml of the seed culture were transferred to 160 ml of the same sterile seed medium in the 500-ml Erlenmeyer flasks. The flasks were shaken on a rotary shaker (220 rpm, 5.1 cm throw) at 25° C. for 2 days, and 640 ml (four flasks) of the second seed culture were inoculated to 20 liters of sterile production medium consisting of modified starch 5%, cottonseed meal 2%, oat meal 0.5%, $KH2PO_4$ 3.5%, $Na_2HPO_4.12H_2O$ 2.63%, $(NH_4)_2SO_4$ 0.6%, L-isoleucine 0.5%, L-proline 0.5%, Adecanol LG-109 0.05%, and Silicone KM-70 0.05% in a 30-liter jar fermentor. Fermentation was carried out at 25° C. for 5 days under aeration of 20 liters/minute and agitation of 250 rpm.

The production of the WF14573A in the fermentation broth was monitored by HPLC analysis indicated below.

analytical HPLC condition; column: YMC Pack ODS-AM 303, S-5 120A (250×4.6 mm I.D., YMC Co., Ltd.); mobile phase: 50% aqueous acetonitrile containing 0.1% TFA; flow rate: 1 m/min. detection: UV at 210 nm; retention time: WF14573A 11.9 min.

(3) Preparation of the Crude WF14573A

The culture broth (80 liters) was extracted with an equal volume of acetone by stirring for 2 hours at room temperature. The mixture was filtered with an aid of diatomaceous earth. The filtrate was diluted with an equal volume of water and passed through a column (6 L) of DIAION HP-20 (Mitsubishi Chemical Co., Ltd.) packed with water. The column was washed with 50% aqueous methanol (19 L) and then eluted with methanol (34 L). The active fraction (0–20 L) was diluted with an equal volume of water and passed through a column (4 L) of YMC-GEL (ODS-AM 120-S50, YMC Co., Ltd.) packed with 50% aqueous methanol. The column was washed with 50% (6.5 L) and 60% (12 L) aqueous methanol and then eluted with 70% aqueous methanol (15.9 L). The active fraction (5.8–15.9 L) was concentrated in vacuo to 5.3 L. A part (4.3 L) of this solution was used to obtain the deacyl WF14573A.

(4) Deacylation of WF14573A

In the 30-liter jar fermentor, 900 ml of 1M sodium phosphate buffer (pH5.8) and 400 g of the vegetative mycelia of *Streptomyces anulatus* No.4811 were added to this solution. The reaction mixture was filled up to 20 L with water. The reaction was carried out at 50° C. with stirring for 2 hours. Decrease of the WF14573A was monitored by analytical HPLC indicated before and increase of the deacyl WF14573A was monitored by analytical HPLC indicated below.

analytical HPLC condition; column: YMC Pack ODS-AM 303, S-5 120A (250×4.6 mm I.D., YMC Co., Ltd.); mobile phase: 6.7% aqueous acetonitrile containing 0.1% TFA; flow rate: 1 m/min. detection: UV at 210 nm; retention time: deacyl WF14573A 8.8 min.

(5) Isolation of the Deacyl WF14573A

The reaction mixture described above was filtered with an aid of diatomaceous earth. The mycelial cake was discarded. The filtrate thus obtained was concentrated in vacuo to 11 L, and passed through a column (1 L) of SEPABEADS SP-207 (Mitsubishi Chemical Co., Ltd.) packed with water. The column was washed with water (3 L) and then eluted with 50% aqueous methanol (3 L). The active fraction (0–2 L) was concentrated in vacuo to an aqueous solution. This solution was passed through a column (2 L) of YMC GEL (ODS-AM 120-S50, YMC Co., Ltd.) packed with water. The column was washed with water and 5% aqueous methanol containing 0.5% $NaH_2PO_4.2H_2O$ (5 L) and 7% aqueous methanol containing 0.5% $NaH_2PO_4.2H_2O$ (3.8 L) and eluted with 10% aqueous methanol containing 0.5% $NaH_2PO_4.2H_2O$ (13.6 L). The active fraction (1.9–11.6 L) was concentrated in vacuo to 3 L. One liter of this solution was passed through a column (2 L) of YMC GEL (ODS-AM 120-S50, YMC Co., Ltd.) packed with water. The column was washed with water and 7% aqueous methanol containing 0.5% $NaH_2PO_4.2H_2O$ (4 L) and eluted with 11% aqueous methanol containing 0.5% $NaH_2PO_4.2H_2O$ (9.2 L). The active fracrion (5.3–6.8 L) was diluted with an equal volume of water and passed through a column (2 L) of YMC GEL (ODS-AM 120-S50) packed with water. The column was washed with water and eluted with 20% aqueous methanol. The eluate was concentrated in vacuo and lyophilized to give 820 mg of the deacyl WF14573A as a white powder. One hundred twenty milligrams of this powder were dissolved in a small volume of water and further purified by preparative HPLC, using YMC-packed column (ODS-AM SH-343-5AM S-5, 250×20 mm I.D., YMC Co., Ltd.) with 11% aqueous methanol containing 0.5% $NaH_2PO_4.2H_2O$ as a mobile phase and a flow rate of 9.9 ml/minute. Active fraction was diluted with an equal volume of water and passed through YMC-packed column (ODS-AM SH-343-5AM S-5, 250×20 mm I.D., YMC Co., Ltd.) equilibrated with water. The column was washed with water (240 ml) and then eluted with 20% aqueous methanol at a flow rate of 9.9 ml/minute. The eluate was concentrated in vacuo and lyophilized to give 67.7 mg of deacyl WF14573A as white powder.

$^1$H NMR spectrum (500 MHz, D2O) δ (ppm): 7.29 (1H, d, 8), 6.86 (1H, d, 2), 6.77 (1H, dd, 8, 2), 5.41 (1H, d, 3), 5.06 (1H, d, 3), 4.94 (1H, d, 6), 4.73 (1H, m), 4.66~4.60 (2H, m), 4.54~4.46 (3H, m),4.40 (1H, m), 4.24~4.19 (2H, m), 4.14~4.07 (2H, m), 3.92 (1H, m), 3.84~3.77 (2H, m), 2.78~2.67 (2H, m), 2.55 (1H, m), 2.46~2.32 (4H, m), 2.15 (1H, m), 2.08~1.99 (2H, m),1.24 (3H, d, 6). $^{13}$C spectrum (125 MHz, D2O) δ (ppm): 176.2 (s), 174.6 (s), 172.24 (s), 172.24 (s), 172.24 (s), 169.7 (s), 169.0 (s), 148.5 (s), 138.2 (s), 137.2 (s), 123.5 (d), 122.1 (d), 118.6 (d), 75.8 (d), 73.1 (d), 72.3 (d), 70.7 (d), 70.6 (d),69.3 (d), 68.0 (d). 67.3 (d), 61.7 (d), 58.0 (d), 57.4 (d), 56.3 (t), 54.8 (d), 53.1 (d), 46.4 (t), 39.8 (t), 39.7 (t), 37.6 (t), 33.1 (t), 31.6 (t), 19.2 (q).

EXAMPLE 4

Preparation of Deacyl WF14573B (1) Fermentation of *Streptomyces anulatus* No. 4811 (FERM BP-5808).

A stock culture of Streptomyces anulatus No.4811 was prepared and maintained on agar slant. A loopful of the slant culture was inoculated into 60 ml of sterilized seed medium consisting of maltose 3%, dried yeast 1%, $CaCO_3$ 0.5% in a 225-ml Erlenmeyer flask. The flask was incubated at 30° C. for 3 days on a rotary shaker (220 rpm, 5.1 cm-throw) and then inoculated (0.1%) into 60 ml of sterilized seed medium consisting of maltose 3%, dried yeast 1%, $CaCO_3$ 0.5%, Adekanol LG-109 (Asahi Denka Co., Ltd.) 0.1% and Silicone KM-70 (Shin-Etsu chemical Co., Ltd.) 0.1% in each of three 225-ml Erlenmeyer flasks. The flasks were incubated at 30° C. for 2 days on a rotary shaker (220 rpm, 5.1 cm-throw).

The resultant seed culture was then inoculated (5%) into 60 ml of sterilized production medium consisting of maltose 8%, soybean meal 2%, wheat germ 2%, potato protein 2%, $CaCO_3$ 0.5%, Adekanol LG-109 0.1% and Silicone KM-70 0.1% in each of fifty 225-ml Erlenmeyer flasks. The flasks were incubated at 30° C. for 6 days on a rotary shaker (220 rpm, 5.1 cm-throw). The vegetative mycelium was collected from the fermented broth by filtration and once washed with water. The washed mycelium was used to obtain the deacyl WF14573B.

(2) Fermentation of *Coleophoma empetri* No. 14573 for the Production of the WF14573B A loopful of the slant culture (*C. empetri* No. 14573) was inoculated into 60 ml of sterilized seed medium consisting of sucrose 4%, glucose 1%, soluble starch 2%, cotton seed flour 3%, soybean powder 1.5%. $KH_2PO_4$ 1%, $CaCO_3$ 0.2%, Adekanol LG-109 0.05% and Silicone KM-70 0.05% in each of three 225-ml Erlenmeyer flasks. The flasks were incubated at 25° C. for 5 days on a rotary shaker (220 rpm, 5.1 cm-throw) and then inoculated (5%) into 160 ml of the same sterilized seed medium in each of twenty 500-ml Erlenmever flasks. The flasks were incubated at 25° C. for 2 davs on a rotary shaker (220 rpm, 5.1 cm-throw).

The resultant seed culture was inoculated (3%) into 20 liters of sterilized production medium in each of five 30-liter jar fermenters. The production medium was composed of sucrose 8%, dried veast 4%, $CaCO_3$ 0.5%, Adekanol LG-109 0.05% and Silicone KM-70 0.05%. The pH was adjusted to 6.3 prior to sterilization. The fermentation was carried out at 25° C. for 5 days under aeration of 20 liters/minute and agitation of 250 rpm.

The production of the WF14573B substance in the fermentation broth was monitored by HPLC analysis indicated below.

analytical HPLC condition; column: YMC Pack ODS-AM 303, S-5 120A (250×4.6 mm I.D., YMC Co., Ltd.); mobile phase: 50% aqueous acetonitrile containing 0.1% TFA; flow rate: 1 m/min. detection: UV at 210 nm; retention time: WF14573B 13.2 min.

(3) Preparation of the Crude WF14573B Substance

After the culture was completed, an equal volume of acetone was added to the cultured broth. The mixture was allowed to stand for about one hour with stirring at room temperature. The resultant mixture was filtrated with an aid of diatomaceous earth. The filtrate was diluted with an equal volume of water and passed through a column (7 L) of DIAION HP-20 (Mitsubishi Chemical Co., Ltd.) packed with water. The column was washed with water (18 L) and 50% aqueous methanol (20 L) and then eluted with methanol (35 L). The eluate was concentrated in vacuo to an aqueous solution. This solution was passed through a column (2 L) of YMC-GEL (ODS-AM 120-S50, YMC Co., LTD.) packed with water. The column was washed with water (6 L) and 50% aqueous methanol (4 L) and then eluted with 80% aqueous methanol (8 L). The elute was concentrated in vacuo to an aqueous solution (600ml).

(4) Deacylation of WF14573B

Thirty ml of 1M Na-phosphate buffer (pH5.8) and 60 g of the vegetative mycelium of *Streptomyces anulatus* No. 4811 (FERM BP-5808) were added to this solution. The reaction was carried out at 50° C. with stirring for 1 hour. Decrease of the WF14573B was monitored by analytical HPLC indicated before and increase of the deacyl WF14573B was monitored by analytical HPLC indicated below.

From 663 mg of the WF14573B, 362 mg of the deacyl WF14573B was formed in the reaction mixture.

analytical HPLC condition; column: YMC Pack ODS-AM 303, S-5 120A (250×4.6 mm I.D., YMC Co., Ltd.); mobile phase: 10% aqueous methanol containing 0.1% TFA; flow rate: 1 m/min. detection: UV at 210 nm; retention time: deacyl WF14573B 11.4 min.

(5) Isolation of the Deacyl WF14573B

The reaction mixture described above was filtrated with an aid of diatomaceous earth. The mycelial cake was discarded. The filtrate thus obtained was passed through a column (150 ml) of SEPABEADS SP-207 (Mitsubishi Chemical Co., Ltd.) packed with water. The column was washed with water (450 ml) and then eluted with 50% aqueous methanol (450 ml). The eluate was concentrated in vacuo to an aqueous solution (100 ml). This solution was passed through a column (180 ml) of YMC GEL (ODS-AM 120-S50, YMC Co., Ltd.) packed with water. The column was washed with water and 5% aqueous methanol containing 0.5% $NaH_2PO_4.2H_2O$ (600 ml) and eluted with 7.5 and 10% aqueous methanol containing 0.5% $NaH_2PO_4.2H_2O$ respectively. The elution was monitored by analytical HPLC indicated before. The portion corresponding to the deacyl WF14573B was concentrated in vacuo to give residual water. This residue was passed through a column (180 ml) of YMC GEL (ODS-AM 120-S50) packed with water. The column was washed with water and 5% aqueous methanol (600 ml) and eluted with 7.5 and 10% aqueous methanol. The eluate was concentrated in vacuo and lyophilized to give 228 mg of the deacyl WF14573B as white powder. Eighty mg of this powder was dissolved in a small volume of water and further purified by preparative HPLC, using YMC-packed column (ODS-AM SH-343-5AM S-5, 250×20 mm I.D., YMC Co., Ltd.) with 12% aqueous methanol containing 0.5% $NaH_2PO_4.2H_2O$ as a mobile phase and a flow rate of 9.9 ml/minute. Fractions containing the deacyl WF14573B were collected and concentrated in vacuo to give residual water. This residue was passed through YMC-packed column (ODS-AM SH-343-5AM S-5, 250×20 mm I.D., YMC Co., Ltd.) equilibrated with water. The column was washed with water (240 ml) and then eluted with 20% aqueous methanol at a flow rate of 9.9 ml/minute. The eluate was concentrated in vacuo and lyophilized to give 41 mg of deacyl WF14573B as white powder.

$^1$H NMR spectrum (500 MHz, D2O) δ (ppm): 7.28 (1H, d, 8), 6.85 (1H, d, 2), 6.76 (1H, dd, 8, 2), 5.40 (1H, d, 3), 5.04 (1H, d, 3), 4.92 (1H, d, 6), 4.72 (1H, m), 4.66~4.60 (2H, m), 4.54~4.47 (2H, m), 4.44~4.37 (2H, m), 4.29 (1H, d, 5), 4.22 (1H, m), 4.10~4.06 (2H, m), 3.93~3.89 (2H, m), 3.42 (1H, m), 2.77~2.66 (2H, m), 2.60~2.50 (2H, m), 2.46~2.35 (3H, m), 2.14 (1H, m), 2.02 (1H, m), 1.24 (3H, d, 7), 1.02 (3H, d, 7). $^{13}$C NMR spectrum (125 MHz, D2O) δ (ppm): 178.4 (s), 176.7 (s), 174.49 (s), 174.45 (s), 174.40 (s), 171.9 (s), 171.4 (s), 150.7 (s), 140.4 (s), 139.4 (s), 125.7 (d), 124.3 (d), 120.8 (d), 78.1 (d), 76.9 (d), 74.5 (d), 72.95 (d), 72.95 (d), 71.4 (d), 69.45 (d), 69.40 (d), 63.9 (d), 60.2 (d), 59.6 (d), 58.5 (t), 57.0 (d), 55.4 (d), 54.9 (t), 42.01 (t), 41.94 (t), 39.85 (d), 39.85 (t), 33.7 (t), 21.4 (q), 13.4 (q).

What is claimed is:

1. A compound of formula (I):

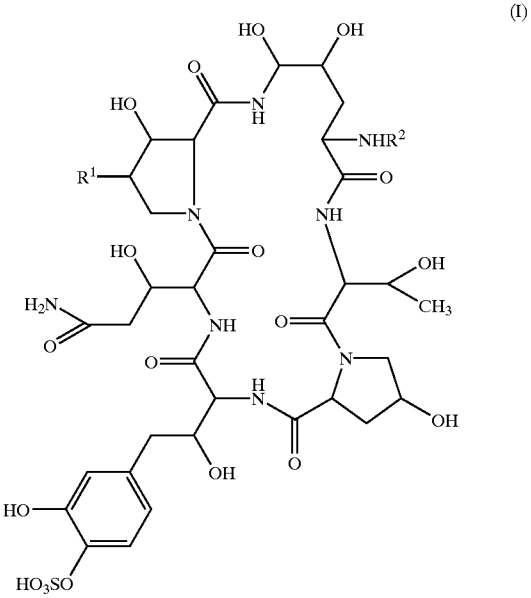

wherein $R^1$ is hydrogen or methyl and $R^2$ is hydrogen or acyl, or a salt thereof.

2. The compound of claim 1, wherein $R^1$ is hydrogen and $R^2$ is palmitoyl.

3. The compound of claim 1, wherein $R^1$ is methyl and $R^2$ is palmitoyl.

4. The compound of claim 1, wherein $R^1$ is hydrogen and $R^2$ is hydrogen.

5. The compound of claim 1, wherein $R^1$ is methyl and $R^2$ is hydrogen.

6. A salt of the compound of claim 1.

7. A composition comprising the compound of claim 1 and optionally, one or more auxiliary agent(s), stabilizing agent(s), thickening agent(s), coloring agent(s), perfume(s), preservative(s) or bacteriostatic agent(s).

8. The composition of claim 7 in combination with a pharmaceutically acceptable carrier or excipient.

9. The composition of claim 7, further comprising one or more auxiliary agent(s), stabilizing agent(s), thickening agent(s), coloring agent(s), or perfume(s).

10. The composition of claim 7, further comprising one or more preservative(s) or bacteriostatic agent(s).

11. The composition of claim 7 in the form of a tablet, pellet, or capsule.

12. The composition of claim 7 in the form of a solution, emulsion or suspension.

13. The composition of claim 7 in the form of a suppository or ointment.

14. A method for inhibiting the growth of a yeast or fungus comprising contacting a yeast or fungus with an amount of the compound of claim 1 effective to inhibit the growth of said yeast or fungus.

15. The method of claim 14, wherein said yeast or fungus is Candida.

16. The method of claim 14, wherein said yeast or fungus is Aspergillus.

17. The method of claim 14, wherein said yeast or fungus is Cryptococcus.

18. A process for producing a compound of formula (I):

wherein $R^1$ is hydrogen or methyl and $R^2$ is hydrogen or palmitoyl, or a salt thereof, comprising:
 (a) culturing a microorganism that produces the compound of formula (I) or a salt thereof, and
 (b) recovering the compound of formula (I) or a salt thereof.

19. The process of claim 18, wherein said microorganism is *Coleophoma*.

20. The process of claim 18, wherein said microorganism is *Coleophoma empetri*.

21. The process of claim 18, wherein said microorganism is *Coleophoma empetri* No. 14573.

22. A process for producing the compound of formula (I):

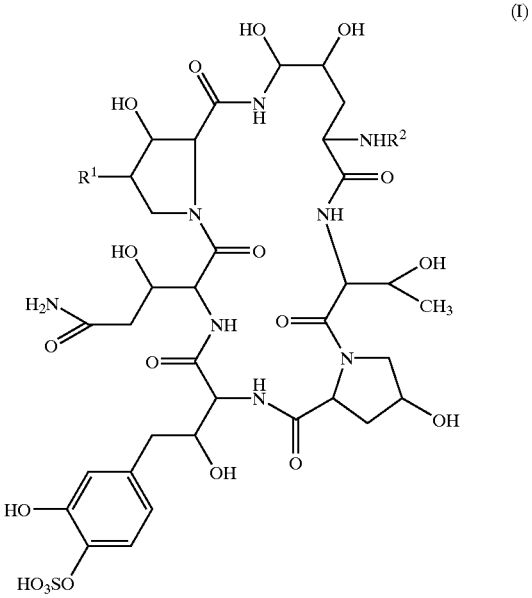

wherein $R^1$ is hydrogen or methyl and $R^2$ is hydrogen, or a salt thereof comprising:
 deacylating a compound of formula (I) by using deacylase, wherein $R^2$ is palmitoyl and
 recovering the compound of formula (I) wherein $R^1$ is hydrogen or methyl and $R^2$ is hydrogen, or a salt thereof.

23. The process of claim 22, comprising contacting said compound of formula (I), wherein $R^2$ is palmitoyl with a microorganism to deacylate said compound.

24. The process of claim 22, comprising contacting said compound of formula (I), wherein $R^2$ is palmitoyl, with Streptomyces to deacylate said compound.

25. The method of claim 14, comprising intravenously administering to a subject in need thereof an amount of said compound effective to inhibit the growth of said yeast or fungus.

26. The method of claim 14, comprising intramuscularly administering to a subject in need thereof an amount of said compound effective to inhibit the growth of said yeast or fungus.

27. The method of claim 14, comprising orally administering to a subject in need thereof an amount of said compound effective to inhibit the growth of said yeast or fungus.

28. The method of claim 14, comprising percutaneously administering to a subject in need thereof an amount of said compound effective to inhibit the growth of said yeast or fungus.

* * * * *